United States Patent
Kawanishi

(10) Patent No.: US 11,047,809 B2
(45) Date of Patent: Jun. 29, 2021

(54) RADIATION IMAGING SYSTEM, RADIATION IMAGING METHOD, CONTROL APPARATUS, AND COMPUTER-READABLE MEDIUM

(71) Applicant: CANON KABUSHIKI KAISHA, Tokyo (JP)

(72) Inventor: Tomohiro Kawanishi, Tachikawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 70 days.

(21) Appl. No.: 16/669,290

(22) Filed: Oct. 30, 2019

(65) Prior Publication Data
US 2020/0141882 A1    May 7, 2020

(30) Foreign Application Priority Data
Nov. 2, 2018   (JP) .............................. JP2018-207505

(51) Int. Cl.
  *G01N 23/04*   (2018.01)
  *A61B 6/00*    (2006.01)
(52) U.S. Cl.
  CPC .............. *G01N 23/04* (2013.01); *A61B 6/52* (2013.01); *A61B 6/467* (2013.01)
(58) Field of Classification Search
  CPC .......... G01N 23/04; A61B 6/52; A61B 6/467; A61B 6/5211; A61B 6/563; A61B 6/463; A61B 6/469; A61B 6/465; A61B 6/4411; A61B 6/5217; A61B 6/461
  See application file for complete search history.

(56) References Cited

U.S. PATENT DOCUMENTS

2016/0247325 A1 *   8/2016   Yu .......................... A61B 6/037

FOREIGN PATENT DOCUMENTS

JP           2013208396 A      10/2013

* cited by examiner

*Primary Examiner* — Courtney D Thomas
(74) *Attorney, Agent, or Firm* — Canon U.S.A., Inc. IP Division

(57) ABSTRACT

A radiation imaging system including an image acquisition unit configured to acquire a radiographic image based on radiation, an image processing setting unit configured to set multiple types of image processing for a specific imaging procedure, an image processing unit configured to perform the multiple of types of image processing set by the image processing setting unit on a radiographic image acquired in the specific imaging procedure to generate multiple radiographic images, and an association setting unit configured to set whether the multiple radiographic images generated by the image processing unit are to be associated with one another.

16 Claims, 12 Drawing Sheets

RADIATION IMAGING SYSTEM, RADIATION IMAGING METHOD, CONTROL APPARATUS, AND COMPUTER-READABLE MEDIUM

BACKGROUND OF THE INVENTION

Field of the Invention

The present disclosure relates to a radiation imaging system, a radiation imaging method, a control apparatus, and a computer-readable medium, and in particular to applying multiple types of image processing to a radiographic image.

Description of the Related Art

In recent years, network-based hospital information systems have been constructed in hospitals. For example, if a radiation imaging of a subject is determined to be necessary, an examination request is input through a HIS (Hospital Information System) terminal. An examination order is then sent to the radiology department, for which the request is intended.

A radiation imaging system performs radiation imaging according to the examination order. A resultant radiographic image may be transferred to a PACS (Picture Archiving and Communication System) or may be output as a printed sheet. The resultant radiographic image may also be subjected to multiple types of image processing. For example, a radiographic image obtained in a pneumoconiosis examination may be subjected to image processing specific to pneumoconiosis, in addition to standard image processing. (For example, see Japanese Patent Application Laid-Open No. 2013-208396.)

In Japanese Patent Application Laid-Open No. 2013-208396, radiographic images are stored in association with examination orders. However, radiographic images resulting from multiple types of image processing are not associated with one another. An operator therefore cannot retrieve, in an associated manner, the radiographic images resulting from the multiple types of image processing.

In view of the above, an aspect of the present disclosure is to provide a radiation imaging system in which radiographic images resulting from multiple types of image processing can be stored in association with one another.

SUMMARY OF THE INVENTION

A radiation imaging system (a control apparatus) according to an aspect of the present disclosure includes: an image acquisition unit configured to acquire a radiographic image based on radiation; an image processing setting unit configured to set multiple types of image processing for a specific imaging procedure; an image processing unit configured to perform the multiple types of image processing set by the image processing setting unit on a radiographic image acquired in the specific imaging procedure to generate multiple radiographic images; and an association setting unit configured to set whether the multiple radiographic images generated by the image processing unit are to be associated with one another.

Further features of the present invention will become apparent from the following description of exemplary embodiments with reference to the attached drawings.

DESCRIPTION OF THE EMBODIMENTS

Preferred embodiments of the present disclosure will now be described in detail in accordance with the accompanying drawings.

First Embodiment

Figure 1:
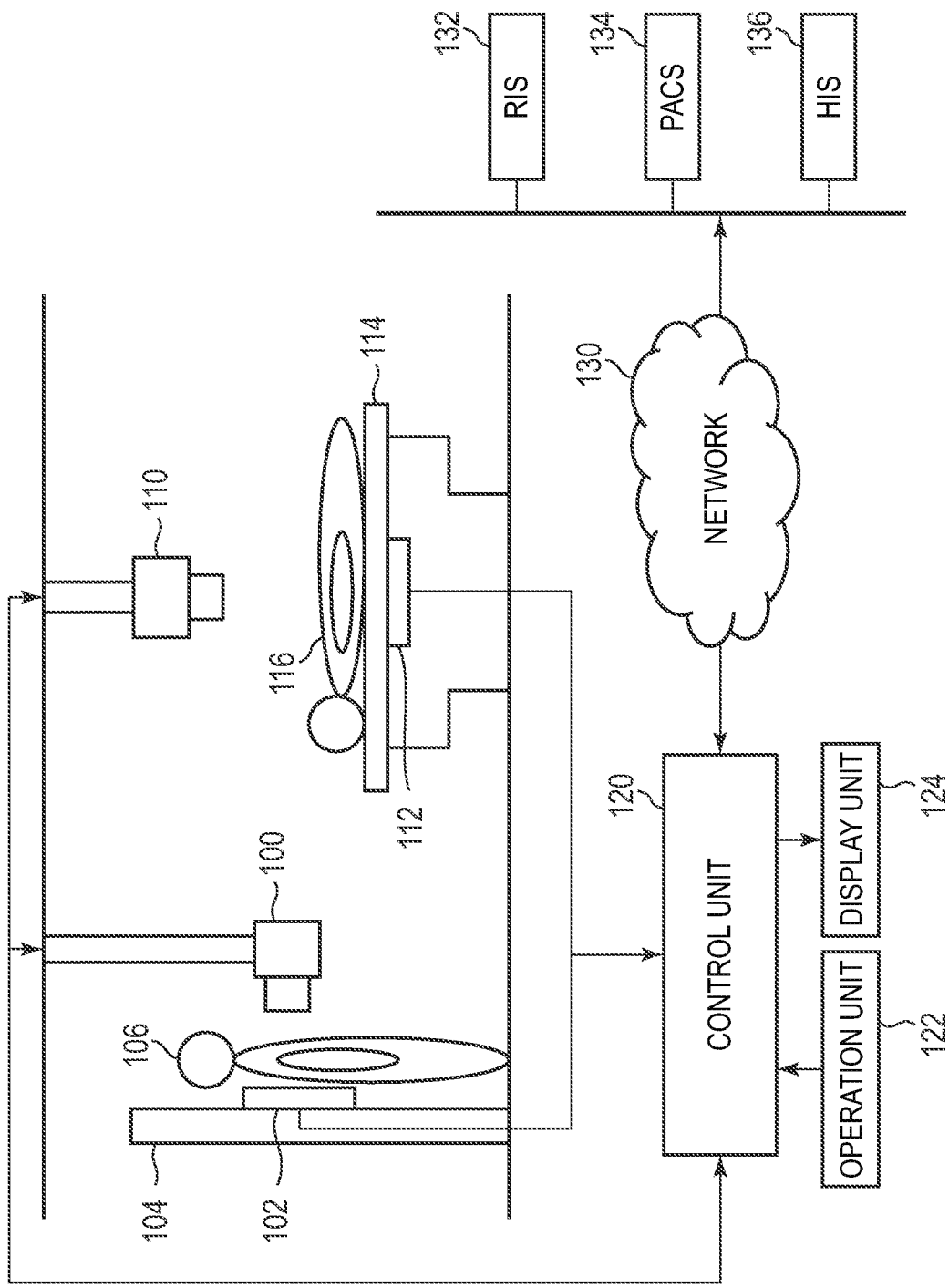
FIG. 1 is a diagram illustrating a general configuration of a radiation imaging system of the present disclosure.

A first embodiment of the present disclosure will be described with reference to FIGS. 1 to 10. As shown in FIG. 1, an imaging room has two sets each including a radiation generator and an imaging platform. Specifically, the imaging room is equipped with a radiation generator 100 that generates radiation, a radiation detector 102 that detects the radiation passing through a subject 106, and an imaging platform 104 that supports the radiation detector 102. The imaging platform 104 is an imaging platform for a standing position. Similarly, the imaging room is equipped with a radiation generator 110 that generates radiation, a radiation detector 112 that detects the radiation passing through a subject 116, and an imaging platform 114 that supports the radiation detector 112. The imaging platform 114 is an imaging platform for a lying position.

A radiation imaging system includes: a display unit 124 that is connected to a control unit 120 and displays radiographic images and various sorts of information; an operation unit 122 used by an operator to perform operations; and the control unit 120. The control unit 120 sets imaging conditions (the tube voltage, the tube current, and the irradiation time) for the radiation generators 100 and 110, processes radiographic images output from the radiation detectors 102 and 112, and performs various sorts of control. The control unit 120 serves as a display control unit for the display unit 124.

The control unit 120 is connected, over a network 130, to an RIS (Radiology Information System) 132 that sends examination orders to the control unit 120, a PACS 134 that manages radiographic images, and an HIS 136 that manages the progress of examinations.

The radiology department in the hospital, upon receiving an examination order through the RIS 132, sends the examination order to the control unit 120 along with radiation imaging information, such as imaging conditions and the imaging procedure. The control unit 120 performs radiation imaging according to the received examination order. The control unit 120 attaches auxiliary information including the examination order to resultant radiographic images and outputs the radiographic images.

The PACS 134 is a server mainly aimed for image management, and includes a storage apparatus for storing radiographic images and auxiliary information. A high-definition monitor connected to the PACS 134 is used to perform operations such as inspection of radiographic images, detailed postprocessing, and diagnosis. Thus, radiographic images output from the control unit 120 are sent to the PACS 134.

The HIS 136 is a hospital management system and includes a server that manages accounting information. When radiation imaging is to be performed, an operator inputs an examination request through a terminal of the HIS 136. The HIS 136 sends the request to the radiology department in the hospital, for which the request is intended. This request information is called an examination order. The examination order includes the name of the requesting department, examination items, and personal data about the subject. Execution information about the examination performed by the radiation imaging system is sent to the HIS 136. The execution information sent to the HIS 136 is used for managing the progress of the examination, as well as for an accounting process after the examination.

The control unit 120, the RIS 132, the PACS 134 and the HIS 136 are interconnected over the network 130 implemented by, for example, a LAN (Local Area Network) or WAN (Wide Area Network).

These apparatuses each include one or more computers. Each computer includes, for example, a main control unit such as a CPU, and a storage apparatus such as ROM (Read Only Memory) or RAM (Random Access Memory). The computer may also include a communication unit such as a network card, and an input-output unit such as a keyboard, display, or touch panel. These components may be interconnected via a bus and are controlled by the main control unit executing programs stored in the storage apparatus.

The control unit 120 is connected to the radiation generators 100 and 110. Specifically, the control unit 120 is connected to the radiation generators 100 and 110 via a wired or wireless network or dedicated line. The control unit 120 sets the radiation imaging conditions on the radiation generators 100 and 110 to control radiation generation by the radiation generators 100 and 110. The radiation generators 110 and 110 serve as radiation sources that generate radiation. The radiation generators 110 and 110 are each implemented by an X-ray tube, for example, and emit radiation toward the respective subjects 106 and 116 (e.g., specific sites of the subjects).

The radiation generators 100 and 110 can irradiate a desired irradiation range with radiation. The radiation generators 100 and 110 are each installed via a support member provided at a floor surface or the ceiling. The irradiation surface of each of the radiation generators 100 and 110 has a diaphragm (not shown) that blocks the radiation. The operator can control the diaphragm that blocks the radiation, thereby defining the irradiation range of the radiation emitted from each of the radiation generators 100 and 110.

The radiation imaging system includes the radiation detectors 102 and 112 that detect the radiation emitted from the respective radiation generators 100 and 110. The radiation detectors 102 and 112 detect the radiation passing through the respective subjects 106 and 116 and output image data according to the radiation. The image data may also be referred to as radiographic images.

Specifically, the radiation detectors 102 and 112 detect the radiation passing through the respective subjects 106 and 116 as electric charges corresponding to the amounts of transmitted radiation. For example, the radiation detectors 102 and 112 may each include a direct-conversion sensor (such as one based on a-Se) that directly converts radiation into electric charges, or an indirect-conversion sensor having a scintillator (such as one based on CsI) and photoelectric conversion elements (such as those based on a-Si). Further, the radiation detectors 102 and 112 each A/D-convert the detected electric charges to generate a radiographic image and output the radiographic image to the control unit 120.

The operation unit 122 is used to operate the radiation imaging system. For example, the operation unit 122 may include a mouse or operation icons, and inputs the operator's instructions to relevant components. The display unit 124 is implemented by a liquid crystal display, for example, and displays various sorts of information to the operator (a radiographer or a medical doctor). The display unit 124 and the operation unit 122 may be integrally implemented as a touch panel.

The control unit 120 is connected to the radiation detectors 102 and 112. Specifically, the control unit 120 is connected to the radiation detectors 102 and 112 via a wired or wireless network or dedicated line. The radiation detectors 102 and 112 image the radiation emitted from the respective radiation generators 100 and 110 and output radiographic images to the control unit 120. The control unit 120 has an application function that runs in the computer. The control unit 120, while controlling the operation of the radiation detectors 102 and 112, outputs the radiographic images and a graphical user interface (GUI) to the display unit 124. The control unit 120 has the function of performing image processing on the radiographic images output from the radiation detectors 102 and 112, such as noise removal, gradation processing, and enhancement processing. The control unit 120 can also perform image processing such as trimming and rotation on the radiographic images output from the radiation detectors 102 and 112. The display unit 124 displays the radiographic images output from the control unit 120.

Figure 2:
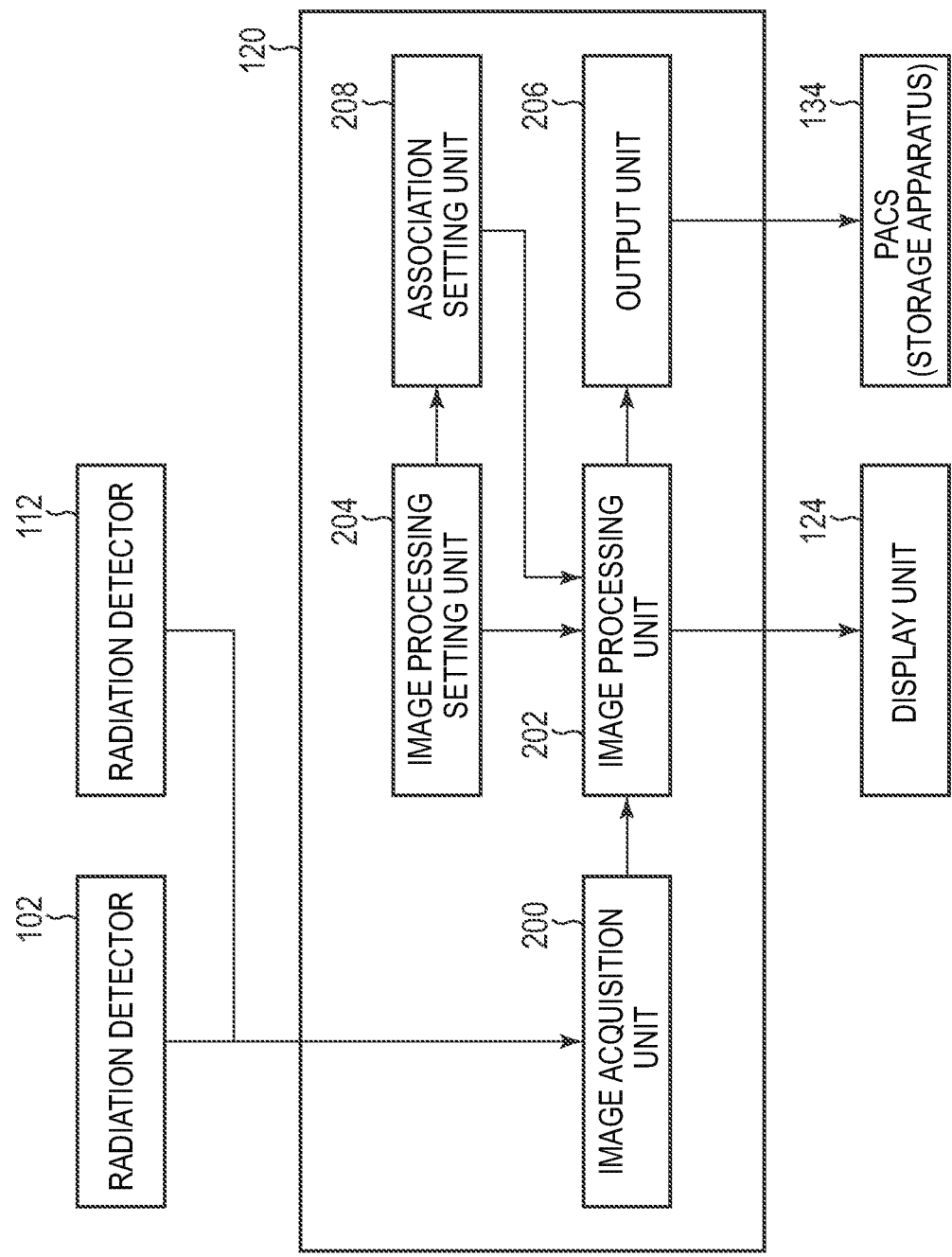
FIG. 2 is a diagram illustrating a configuration of a control unit in the radiation imaging system of the present disclosure.

Here, details of the control unit 120 will be described with reference to FIG. 2. As shown in FIG. 2, the control unit 120 includes: an image acquisition unit 200 that acquires a radiographic image (image data) output from each of the radiation detectors 102 and 112; an image processing unit 202 that performs image processing on the radiographic image acquired by the image acquisition unit 200; an image processing setting unit 204 that sets the image processing to be performed by the image processing unit 202; an output unit 206 that outputs radiographic images resulting from the image processing performed by the image processing unit 202 to an external apparatus (the PACS (the storage apparatus)); and an association setting unit 208 that associates the radiographic images resulting from the image processing performed by the image processing unit 202 with one another. The control unit 120 performs these processes by causing the computer to execute programs stored in the memory (ROM or RAM).

The control unit 120 causes the display unit 124 to display the radiographic images output from the image processing unit 202. The display unit 124 displays the radiographic images processed and output by the image processing unit 202. The display unit 124 may also display image processing setting information related to the image processing setting unit 204, and association setting information related to the association setting unit 208. This allows the operator to know which types of image processing are performed by the image processing unit 202 and where the output unit 206 outputs the radiographic images. The operator can modify, through the operation unit 122, the image processing setting information related to the image processing setting unit 204 and the association setting information related to the association setting unit 208.

The PACS (the storage apparatus) 134 stores the radiographic images output from the output unit 206. The PACS (the storage apparatus) 134 stores radiographic images resulting from multiple types of image processing performed by the image processing unit 202. The PACS (the storage apparatus) 134 may store the radiographic images along with information such as image processing information and subject information.

The image processing unit 202 can perform multiple types of image processing on a radiographic image based on image processing information set by the image processing setting unit 204. That is, the image processing unit 202 can set (add) the types of image processing for a single radiographic image. For example, the image processing unit 202 subjects a radiographic image to normal image processing, black-and-white reversal processing, and pneumoconiosis-specific processing, thereby generating multiple radiographic images. The normal image processing is to subject a radiographic image output from the image acquisition unit 200 to processing such as gradation conversion for converting pixel values into intensity (luminance) values. The black-and-white reversal processing is to invert the intensity (luminance) values (black and white) of the radiographic image resulting from the normal image processing. The black-and-white reversal processing is effective for enhancing white and gray portions in areas displayed in black in the radiographic image resulting from the normal image processing. The pneumoconiosis-specific processing is to apply predetermined image processing for pneumoconiosis to generate a radiographic image separately from the radiographic image resulting from the normal image processing. Specifically, the pneumoconiosis-specific processing is different from the normal image processing in image processing parameters for frequency-component-based gradation conversion, luminance, contrast, edge enhancement, and noise removal.

The normal image processing may also be called first image processing, and image processing such as the black-and-white reversal processing and the pneumoconiosis-specific processing may also be called second image processing. That is, the image processing unit 202 can subject a single radiographic image to the first image processing (the normal image processing) and the second image processing (the additional image processing) to generate multiple radiographic images.

In this embodiment, the image processing unit 202 applies the black-and-white reversal processing and the pneumoconiosis-specific processing to generate radiographic images separately from the radiographic image resulting from the normal image processing. That is, the image processing unit 202 generates the radiographic image resulting from the normal image processing, and the radiographic image resulting from at least one of the black-and-white reversal processing and the pneumoconiosis-specific processing.

The image processing unit 202 stores one or more image processing parameters for each imaging procedure. For example, one or more image processing parameters are stored for each type of imaging, such as chest front-view imaging, chest side-view imaging, abdomen front-view imaging, and abdomen side-view imaging. For chest front-view imaging, three image processing parameters related to the normal image processing, the black-and-white reversal processing, and the pneumoconiosis-specific processing are stored. For abdomen front-view imaging, only two image processing parameters related to the normal image processing and the black-and-white reversal processing are stored, because the pneumoconiosis-specific processing is not required. The operator can set the types of image processing for each imaging procedure through the image processing setting unit 204.

The association setting unit 208 sets whether the radiographic images resulting from the multiple types of image processing are to be associated with one another. The association setting unit 208 may also be called a grouping unit that groups the radiographic images resulting from the multiple types of image processing into a certain group. The image processing unit 202 subjects a single radiographic image to the first image processing (the normal image processing) and the second image processing (the additional image processing) to generate multiple radiographic images. The association setting unit 208 can then associate the radiographic images, resulting from performing the multiple types of image processing on the single radiographic image, with one another. This association is possible because the radiographic images resulting from the multiple types of image processing share the original image (the source image).

Specifically, to associate the radiographic images resulting from the multiple types of image processing with one another, the association setting unit 208 assigns the same auxiliary information (tag) to the radiographic images resulting from the multiple types of image processing. That is, the same auxiliary information (tag) can be assigned to the radiographic images resulting from performing the first image processing (the normal image processing) and the second image processing (the additional image processing) on the single radiographic image.

The association setting unit 208 can also set that the radiographic images resulting from the multiple types of image processing be dissociated from one another. If the radiographic images resulting from the multiple types of image processing are to be dissociated from one another, the association setting unit 208 assigns different auxiliary information (a different tag) to each of the radiographic images resulting from the multiple types of image processing.

Figure 3:
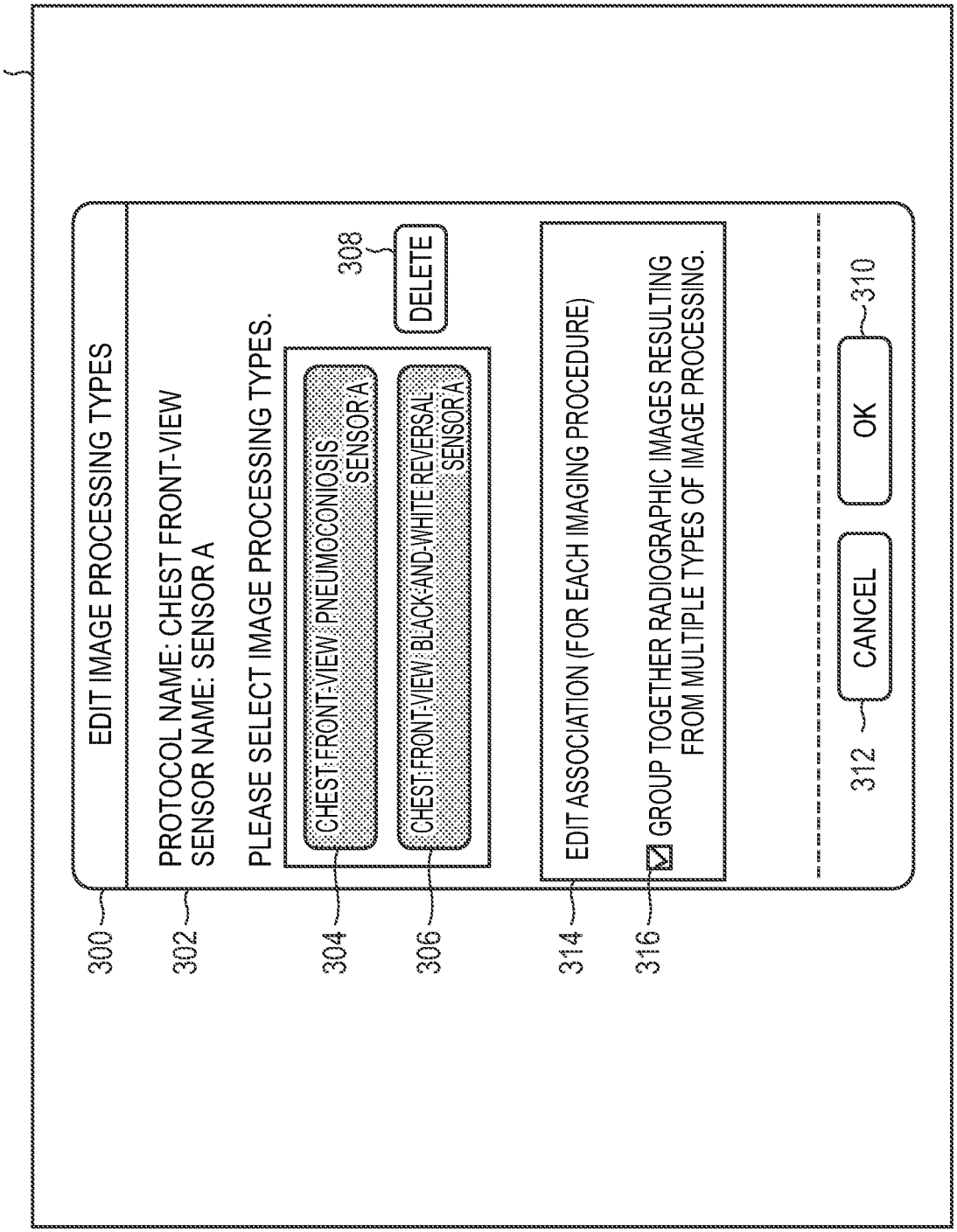
FIG. 3 is a diagram illustrating an exemplary setting screen for an image processing setting unit and an association setting unit in the radiation imaging system of the present disclosure.

FIG. 3 illustrates a setting screen for the image processing setting unit 204 and the association setting unit 208, displayed on the display unit 124. The setting screen for the image processing setting unit 204 and the association setting unit 208 is displayed on the display unit 124. Icons are selected through the operation unit 122 to perform relevant operations.

As shown in FIG. 3, an "Edit image processing types" menu 300 shows: an imaging procedure (the protocol name and the sensor name) 302; image processing icons 304 and 306 for selecting image processing available for the imaging procedure; a delete icon 308 for deleting a selected image processing icon; an OK icon 310 for confirming multiple types of image processing and the setting in an "Edit association" menu for the imaging procedure; and a cancel icon 312 for cancelling multiple types of image processing and the setting in the "Edit association" menu for the imaging procedure.

The "Edit association" menu 314 shows an association setting icon 316 for setting whether the radiographic images resulting from the multiple types of image processing are to be grouped together.

In the "Edit image processing types" menu 300, the image processing icons 304 and 306 for additional image processing are displayed. No image processing icon is displayed for the normal image processing, because the normal image processing is performed on all radiographic images and therefore need not be selected.

In this embodiment, "protocol name: chest front-view, sensor name: sensor A" is displayed as the imaging procedure (the protocol name and the sensor name) 302. The operator can use the operation unit 122 to change the imaging procedure (the protocol name and the sensor name) as appropriate. The image processing setting unit 204 can set the types of image processing on an imaging-procedure basis. The image processing information set by the image processing setting unit 204 is sent to the image processing unit 202.

For the imaging procedure shown in FIG. 3, the icon 304 for performing the pneumoconiosis-specific processing and the icon 306 for performing the black-and-white reversal processing are displayed. The operator can press the icon 304 for performing the pneumoconiosis-specific processing, thereby causing the image processing unit 202 to generate a radiographic image resulting from the predetermined image processing for pneumoconiosis, in addition to a radiographic image resulting from the normal image processing. Pressing the icon 304 for performing the pneumoconiosis-specific processing changes the display style of the icon 304 (e.g., the color or border of the icon 304), allowing the operator to recognize that the icon 304 for performing the pneumoconiosis-specific processing is pressed.

The operator can press the icon 306 for performing the black-and-white reversal processing, thereby causing the image processing unit 202 to generate a radiographic image resulting from the processing of inverting the intensity (luminance) values (black and white) of the radiographic image resulting from the normal image processing. Pressing the icon 306 for the black-and-white reversal processing changes the display style of the icon (e.g., the color or border of the icon), allowing the operator to recognize that the icon 306 for performing the black-and-white reversal processing is pressed. For example, for the display style of the icons 304 and 306 shown in FIG. 3, the colors of the icon 304 for performing the pneumoconiosis-specific processing and the icon 306 for performing the black-and-white reversal processing have been changed. The operator can thus recognize that the types of image processing corresponding to the respective icons 304 and 306 are selected.

While this embodiment describes that the pneumoconiosis-specific processing and the black-and-white reversal processing are selectable for chest front-view imaging, this is not limiting. Various other types of image processing may be selectable, such as noise reduction, edge enhancement, vertical flipping, horizontal flipping, scaling up, and scaling down.

The "Edit association" menu 314 is set for each imaging procedure (the protocol name and the sensor name). In this embodiment, as shown in FIG. 3, the multiple types of image processing are determined to be performed on a radiographic image obtained according to "protocol name: chest front-view, sensor name: sensor A." Then, this menu allows setting whether the radiographic images resulting from the multiple types of image processing are to be associated with one another.

In the "Edit association" menu 314, the association setting icon 316 is made selectable if multiple types of image processing are to be performed for a single radiographic image. In this embodiment, as shown in FIG. 3, the function of the "Edit association" menu 314 (the association setting icon 316) is made selectable if the icon 304 for performing the pneumoconiosis-specific processing or the icon 306 for performing the black-and-white reversal processing is pressed.

The "Edit association" menu 314 displays the association setting icon 316 for setting whether to group together the radiographic images resulting from the multiple types of image processing. The association setting icon 316 in the "Edit association" menu 314 is made selectable if the icon 304 for performing the pneumoconiosis-specific processing or the icon 306 for performing the black-and-white reversal processing is pressed.

Checking the box of the association setting icon 316 enables the setting of associating the radiographic images resulting from the multiple types of image processing with one another as a group. Unchecking the box of the association setting icon 316 results in that the radiographic images resulting from the multiple types of image processing are dissociated from one another as separate groups. The operator can then press the OK icon 310 for confirming the setting of the multiple types of image processing and the association edit setting for this imaging procedure, so that these settings take effect.

In FIG. 3, the icon 304 for performing the pneumoconiosis-specific processing and the icon 306 for performing the black-and-white reversal processing are pressed, so that the pneumoconiosis-specific processing and the black-and-white reversal processing are selected for chest front-view imaging. The radiographic image generated in the normal image processing is subjected to the predetermined image processing for pneumoconiosis and the processing of inverting the intensity (luminance) values (black and white) to generate respective radiographic images. Since the box of the association setting icon 316 is checked, the setting of associating the radiographic images resulting from the multiple types of image processing with one another as a group is enabled. Therefore, the radiographic images resulting from the normal image processing, the predetermined image processing for pneumoconiosis, and the processing of inverting the intensity (luminance) values (black and white) are associated with one another. That is, the same auxiliary information (tag) can be assigned to the radiographic images resulting from the normal image processing, the predetermined image processing for pneumoconiosis, and the processing of inverting the intensity (luminance) values (black and white).

If only the pneumoconiosis-specific processing is selected for chest front-view imaging, the radiographic image resulting from the normal image processing is subjected to the predetermined image processing for the pneumoconiosis to generate a radiographic image. If, then, the box of the association setting icon 316 is checked, the setting of associating the radiographic images resulting from the multiple types of image processing with one another as a group is enabled. Therefore, the radiographic images resulting from the normal image processing and the predetermined image processing for pneumoconiosis are associated with one another. The same auxiliary information (tag) can be assigned to the radiographic images resulting from the normal image processing and the predetermined image processing for pneumoconiosis. Thus, the same auxiliary information (tag) can be assigned to the radiographic images resulting from the image processing selected in the "Edit image processing types" menu.

The association setting icon 316 may be the reverse of the above-described setting function. For example, the association setting icon 316 may allow setting whether to separate the radiographic images resulting from the multiple types of image processing into different groups. In this case, checking the box of the association setting icon 316 enables the setting of dissociating the radiographic images resulting from the multiple types of image processing from one another as different groups. Unchecking the box of the association setting icon 316 enables the setting of associating the radiographic images resulting from the multiple types of image processing with one another as a group.

Figure 4:
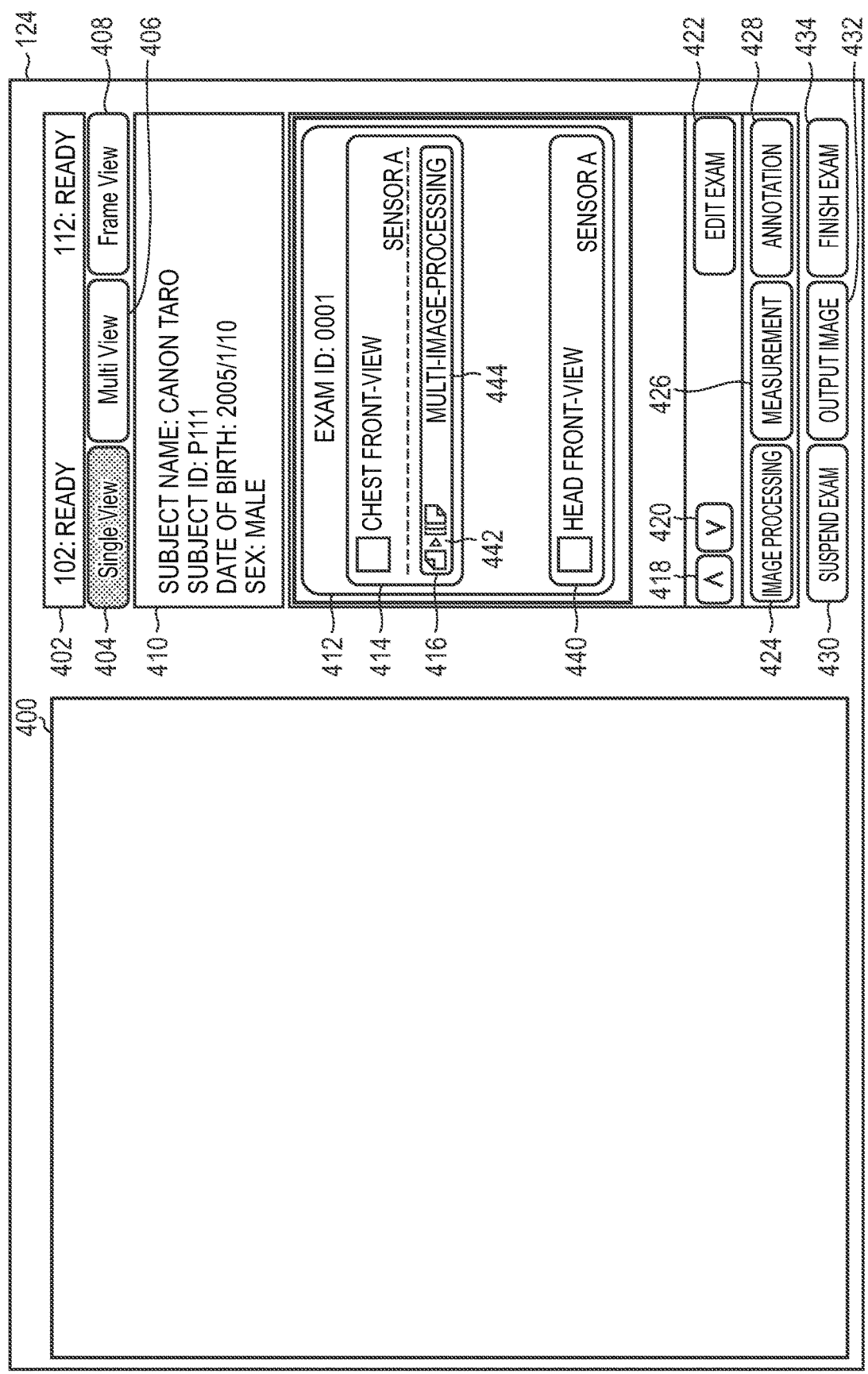
FIG. 4 is a diagram illustrating an exemplary display screen before imaging in the radiation imaging system of the present disclosure.

FIG. 4 illustrates a display screen of the display unit 124 before imaging. The control unit 120 can control the display screen of the display unit 124. The display screen of the display unit 124 includes an image display area 400 for displaying radiographic images. The display screen of the display unit 124 includes a status display area 402 for displaying the statuses of the radiation detectors 102 and 112, a single-view icon 404, a multi-view icon 406, and a frame-view icon 408.

The display screen of the display unit 124 includes a subject display area 410 for displaying information about the subject, and an examination information display area 412 for displaying information about the examination. The examination information display area 412 includes imaging procedure icons 414 and 440 for displaying and performing imaging procedures, and a multi-image-processing display area 416 for indicating that multiple types of image processing are specified for the corresponding imaging procedure. The imaging procedure icons 414 and 440 may also be called imaging protocols.

The display screen of the display unit 124 includes a move up icon 418, a move down icon 420, an edit exam icon 422, an image processing icon 424, a measurement icon 426, an edit annotation icon 428, a suspend exam icon 430, an output image icon 432, and a finish exam icon 434.

The image display area 400 displays a radiographic image captured. Switching the display target after imaging causes another selected radiographic image to be displayed. The image display area 400 may also display information such as subject information, examination information, and imaging conditions, as necessary.

The status display area 402 is an area that displays the statuses of the radiation detectors 102 and 112 with different colors and character types for easy recognition by the operator. Since the radiation imaging system has the two radiation detectors 102 and 112 as shown in FIG. 1, two status display areas 402 may be displayed for indicating the respective statuses of the radiation detectors 102 and 112.

The control unit 120 receives the statuses from the radiation detectors 102 and 112 and sends the statuses to the display unit 124. For example, if the radiation detectors 102 and 112 are not ready for detection, "Not Ready" is displayed in the status display area 402. If the radiation detectors 102 and 112 are ready for detection, "Ready" is displayed in the status display area 402. The background color of "Ready" is changed to a color distinguishable from the background color of "Not Ready."

The single-view icon 404 is an icon for switching to single view, in which a single radiographic image frame being selected is displayed in the image display area 400. For a multi-frame image, the operation unit 122 may be operated during preview display to display another frame or to play frames as a video. The multi-view icon 406 is an icon for switching to multi view, in which a group of images captured in the current examination is simultaneously displayed in the image display area 400 divided into a grid of display subareas. The frame-view icon 408 is an icon for switching to frame view, in which a group of frame images of a video is simultaneously displayed in the image display area 400 divided into a grid of display subareas.

The subject display area 410 displays information about the subject, such as the subject's name, ID, date of birth, and sex. The examination information display area 412 displays the examination ID related to imaging, and the imaging procedure icons 414 and 440 indicating imaging procedures. The imaging procedure icons 414 and 440 each show an imaging procedure, including information such as the imaging procedure name and the radiation detector name, and also show the thumbnail of a radiographic image if the imaging is finished. If the imaging is not started yet, a thumbnail indicating the imaging posture is displayed. The thumbnail indicating the imaging posture includes information about the imaging platform 104 or 114 supporting the radiation detector 102 or 112. The operator can thus see the thumbnail display to know whether the imaging according to each imaging procedure has been performed.

In this embodiment, the imaging procedure (chest front-view) of the imaging procedure icon 414 involves multiple types of image processing to be performed on a radiographic image captured in the imaging procedure of the imaging procedure icon 414. By contrast, the imaging procedure (head front-view) of the imaging procedure icon 440 involves not multiple types of but only the normal image processing to be performed on a radiographic image captured in the imaging procedure of the imaging procedure icon 440. The imaging procedure icons 414 and 440 are therefore displayed in a manner that allows distinction about whether multiple types of image processing are performed or not.

The imaging procedure icon 414 involving multiple types of image processing shows the multi-image-processing display area 416. The multi-image-processing display area 416 includes a multi-image-processing icon 442 and text information 444, both indicating that multiple types of image processing are performed. The text information 444 reads "multi-image-processing," for example. The multi-image-processing icon 442 includes a leftward image representing a single radiographic image, and a rightward image representing the generation of multiple (e.g., three) radiographic images. That is, the multi-image-processing icon 442 indicates performing multiple types of image processing on a single radiographic image to generate multiple radiographic images. Because of the multi-image-processing display area 416 displayed inside the imaging procedure icon 414, the imaging procedure icon 414 involving multiple types of image processing is displayed larger than the imaging procedure icon 440 involving a single type of image processing. The imaging procedure icon 414 involving multiple types of image processing may be displayed in a different color or shape, or in any manner that allows the operator to recognize that multiple types of image processing are performed.

The control unit 120 thus causes the display unit 124 to display the information about multiple types of image processing in the imaging procedure icon 414 corresponding to the specific imaging procedure. The display unit 124 can accordingly display the information about multiple types of image processing in the imaging procedure icon 414 corresponding to the specific imaging procedure (chest front-view).

The control unit 120 may cause the display unit 124 to display either one of the multi-image-processing icon 442 and the text information 444, both indicating that multiple types of image processing are performed. The display unit 124 may display either one of the multi-image-processing icon 442 and the text information 444, both indicating that multiple types of image processing are performed.

If image processing such as the black-and-white reversal processing and the pneumoconiosis-specific processing are set by the image processing setting unit 204 in addition to the normal image processing, the multi-image-processing display area 416 indicates that the multiple types of image processing are set. Specifically, if the image processing setting unit 204 sets multiple types of image processing for the chest front-view imaging procedure, the control unit 120 notifies the display unit 124 that the multiple types of image processing are set for the chest front-view imaging procedure. The display unit 124 displays the multi-image-processing display area 416 in the imaging procedure icon 414 for the chest front-view imaging procedure.

The operator can see the multi-image-processing display area 416 to recognize that multiple types of image processing are set for the imaging procedure displayed in the imaging procedure icon 414. Here, the operator can recognize that multiple types of image processing are set for the chest front-view imaging procedure. The operator can also recognize that only the normal image processing is set for the head front-view imaging procedure.

The move up icon 418 is an icon for instructing to move up an imaging procedure in the order of the imaging procedures to be performed. The move down icon 420 is an icon for instructing to move down the imaging procedure in the order of the imaging procedures to be performed. The edit exam icon 422 is an icon for instructing to transition to a screen such as the setting screen for the image processing setting unit 204 and the association setting unit 208 shown in FIG. 3, for example. The image processing icon 424 is an icon for instructing to display or hide image processing results. The measurement icon 426 is an icon for instructing to display or hide measurement operation functions. The edit annotation icon 428 is an icon for instructing to display or hide annotations. The suspend exam icon 430 is an icon for instructing to suspend the current examination. The output image icon 432 is an icon for instructing to output a radiographic image obtained in the current examination. The finish exam icon 434 is an icon for receiving an operation input for finishing the examination that includes at least one imaging operation.

Figure 5:
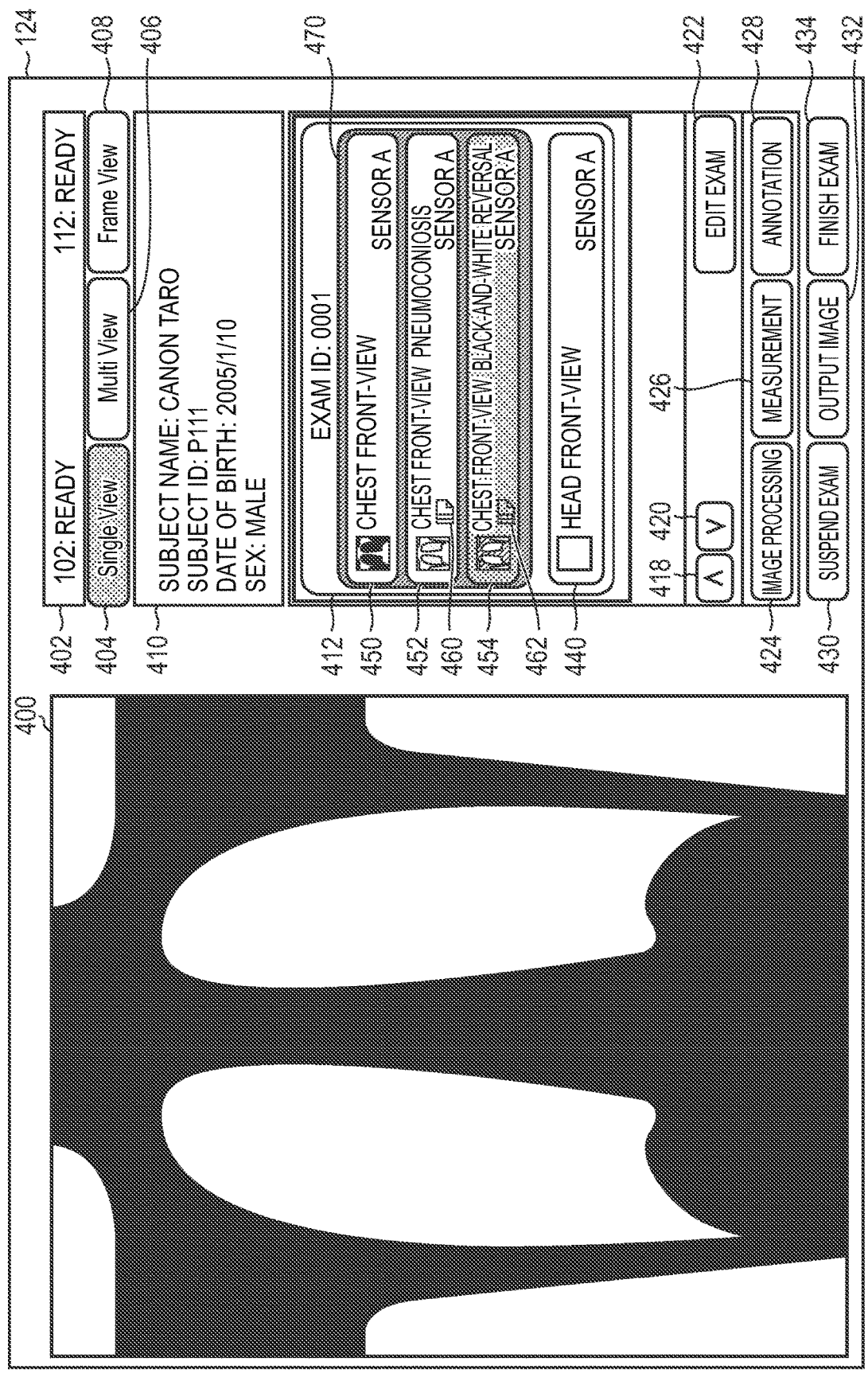
FIG. 5 is a diagram illustrating an exemplary display screen after imaging in the radiation imaging system of the present disclosure.

FIG. 5 illustrates a display screen of the display unit 124 after imaging is performed according to the specific imaging procedure involving multiple types of image processing. What are different from the display screen of the display unit 124 shown in FIG. 4 are the image display area 400 and the examination information display area 412.

In FIG. 4, multiple types of image processing are set for the chest front-view imaging procedure, so that the multi-image-processing display area 416 is displayed.

Performing the chest front-view imaging procedure involving the multiple types of image processing results in the display as shown in FIG. 5. A radiographic image captured is displayed in the image display area 400. The imaging procedure icon 414 representing the chest front-view imaging procedure shown in FIG. 4 is decomposed (expanded) into imaging procedure icons 450, 452 and 454 for the respective types of image processing. Here, since the pneumoconiosis-specific processing and the black-and-white reversal processing are set by the image processing setting unit 204, the three imaging procedure icons 450, 452 and 454 for the normal image processing, the pneumoconiosis-specific processing, and the black-and-white reversal processing are displayed.

The imaging procedure icon 450 is an icon corresponding to the normal image processing. The imaging procedure icon 450 contains the thumbnail of a radiographic image resulting from the normal image processing. The imaging procedure icon 452 is an icon corresponding to the pneumoconiosis-specific processing. The imaging procedure icon 452 contains a variation mark 460 indicating that a variation has been created by applying image processing different from the normal image processing. The imaging procedure icon 452 contains the thumbnail of a radiographic image resulting from the pneumoconiosis-specific processing. The imaging procedure icon 454 is an icon corresponding to the black-and-white reversal processing. The imaging procedure icon 454 contains a variation mark 462 indicating that a variation has been created by applying image processing different from the normal image processing. The imaging procedure icon 454 contains the thumbnail of a radiographic image resulting from the black-and-white reversal processing.

The variation marks 460 and 462 are thus displayed in the imaging procedure icons 452 and 454, indicating that the multiple types of image processing have been applied to create the variations of the radiographic image.

Identification information 470 is displayed for the imaging procedure icons corresponding to the multiple types of image processing, indicating that these icons belong to the same imaging procedure. The identification information 470 is displayed to surround the imaging procedure icons. This allows the operator to recognize that the imaging procedure icons 450, 452 and 454 corresponding to the normal image processing, the pneumoconiosis-specific processing, and the black-and-white reversal processing belong to the same imaging procedure. The identification information 470 may take any form, such as text, a symbol, or an indicator, that allows the operator to recognize that the icons belong to the same imaging procedure.

After the specific imaging procedure involving the multiple types of image processing is performed, the image display area 400 displays the radiographic image corresponding to the imaging procedure icon 454 located at the bottom among the imaging procedure icons 450, 452 and 454. Because the imaging procedure icon 454 is the icon corresponding to the black-and-white reversal processing, the radiographic image resulting from the black-and-white reversal processing is displayed in the image display area 400. The imaging procedure icon 454 corresponding to the radiographic image displayed in the image display area 400 has its display style (such as the color or the shape) changed. The operator can therefore recognize that the radiographic image resulting from the black-and-white reversal processing is being displayed, because the imaging procedure icon 454 is the icon corresponding to the black-and-white reversal processing.

No radiographic image is displayed in the thumbnail area of the imaging procedure icon 440, suggesting that imaging has not been performed yet. Because only the normal image processing is to be performed in the imaging procedure (head front-view) of the imaging procedure icon 440, the imaging procedure icon 440 will not be decomposed (expanded) after imaging; a radiographic image will be displayed in the thumbnail area of the imaging procedure icon 440. The imaging procedure icon 440 does not involve multiple types of image processing and therefore has no identification information 470 indicating icons belonging to the imaging procedure.

It is to be noted that the multiple types of image processing may be performed after the normal image processing is performed by the image processing unit 202 and the resultant radiographic image is displayed on the display unit 124. Specifically, the radiographic image resulting from the normal image processing is displayed in the image display area 400 of the display unit 124. At this point, the thumbnail of the radiographic image resulting from the normal image processing is displayed in the imaging procedure icon 414. If the operation unit 122 is used to select the multi-image-processing icon 442 indicating that multiple types of image processing are performed, the image processing unit 202 performs the multiple types of image processing, for example the pneumoconiosis-specific processing and the black-and-white reversal processing. The display unit 124 then displays the imaging procedure icon 452 corresponding to the pneumoconiosis-specific processing, and the imaging procedure icon 454 corresponding to the black-and-white reversal processing. The display unit 124 can display radiographic images resulting from the pneumoconiosis-specific processing and the black-and-white reversal processing. Thus, with a single operation of pressing the multi-image-processing icon 442, multiple types of image processing can be performed on a single radiographic image to display the respective radiographic images.

Figure 6:
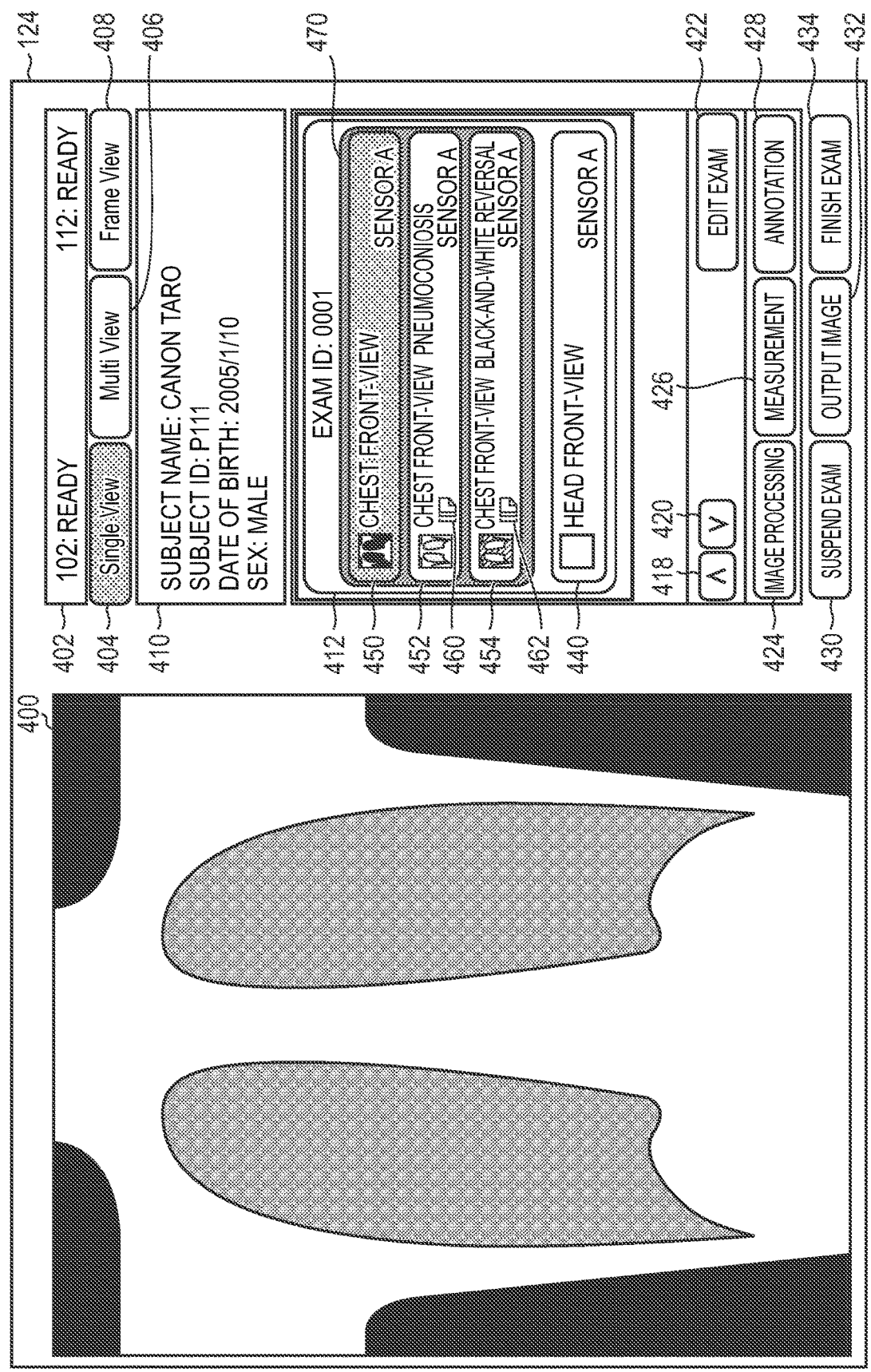
FIG. 6 is a diagram illustrating an exemplary display screen after imaging in the radiation imaging system of the present disclosure.

FIG. 6 illustrates a display screen of the display unit 124 after imaging is performed according to the specific imaging procedure involving the multiple types of image processing. In FIG. 5, the image display area 400 displays the radiographic image corresponding to the imaging procedure icon 454 located at the bottom among the imaging procedure icons 450, 452 and 454. Here, the radiographic image displayed in the image display area 400 can be changed. The operator can select the imaging procedure icon 450 through the operation unit 122 to cause the display unit 124 to display the radiographic image resulting from the normal image processing. The operator can select the imaging procedure icon 452 through the operation unit 122 to cause the display unit 124 to display the radiographic image resulting from the pneumoconiosis-specific processing.

In FIG. 6, the radiographic image corresponding to the imaging procedure icon 450 is displayed. The imaging procedure icon 450 corresponding to the radiographic image displayed in the image display area 400 has its display style (such as the color or the shape) changed. The operator can therefore recognize that the radiographic image resulting from the normal image processing (the original image (the source image)) is being displayed, because the imaging procedure icon 450 is the icon corresponding to the normal image processing.

Figure 7:
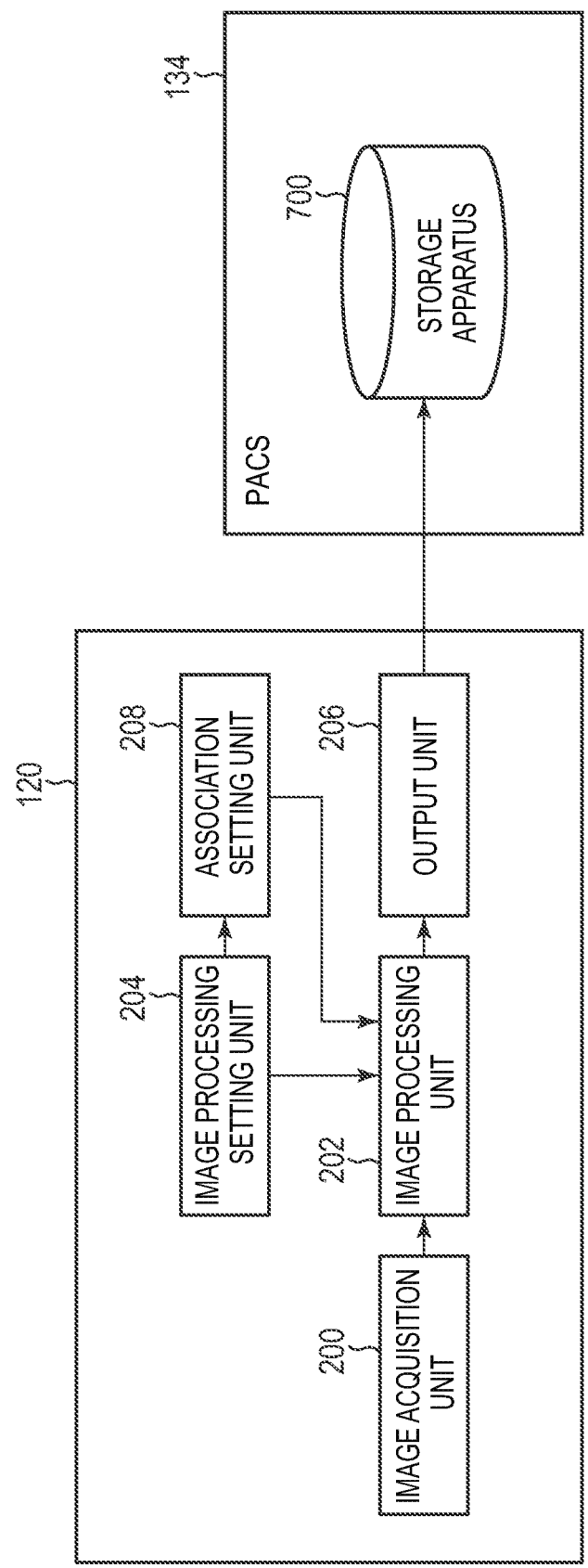
FIG. 7 is a diagram illustrating an exemplary output configuration in the radiation imaging system of the present disclosure.

FIG. 7 is a diagram illustrating a configuration of outputting radiographic images in the radiation imaging system.

The image processing unit 202, separately from the radiographic image resulting from the normal image processing, generates radiographic images by applying processing such as the black-and-white reversal processing and the pneumoconiosis-specific processing. The image processing unit 202 then sends, to the output unit 206, the radiographic image resulting from the normal image processing, the radiographic image resulting from the black-and-white reversal processing, and the radiographic image resulting from the pneumoconiosis-specific processing. In this embodiment, the image processing unit 202 sends these radiographic images to the output unit 206 along with image processing information about the normal image processing, the black-and-white reversal processing, and the pneumoconiosis-specific processing.

Also, once the image processing setting unit 204 sets the image processing other than the normal image processing, image processing information about the set image processing is sent to the association setting unit 208. For example, if the image processing setting unit 204 sets the black-and-white reversal processing and the pneumoconiosis-specific processing, the image processing setting unit 204 sends image processing information about the black-and-white reversal processing and the pneumoconiosis-specific processing to the association setting unit 208. That is, image processing information about the image processing set (added) by the image processing setting unit 204 is sent to the association setting unit 208. Image processing information about the normal image processing need not be sent to the association setting unit 208, because the normal image processing is performed on all radiographic images.

The association setting unit 208 receives the image processing information about the image processing set (added) by the image processing setting unit 204 and sets whether the radiographic images resulting from the multiple types of image processing are to be associated with one another as a group. If the radiographic images resulting from the multiple types of image processing are to be associated with one another, the same auxiliary information (tag) is assigned to the radiographic images resulting from the multiple types of image processing.

The PACS 134 has a storage apparatus 700 that stores all radiographic images captured in the radiation imaging system (including radiographic images resulting from the normal image processing). The output unit 206 outputs the radiographic images to the PACS 134 along with the auxiliary information. The PACS 134 stores the radiographic images output from the output unit 206. If the radiographic images resulting from the multiple types of image processing are associated with one another, the PACS 134 stores, along with the same auxiliary information, the radiographic images resulting from the multiple types of image processing performed by the image processing unit 202.

Thus, since the radiographic images resulting from the multiple types of image processing are stored in the storage apparatus 700 along with the same auxiliary information, the operator can efficiently search for a radiographic image by the auxiliary information. For example, when searching for the radiographic image resulting from the pneumoconiosis-specific processing, the operator can simultaneously search for the radiographic image resulting from the normal image processing.

Figure 8:
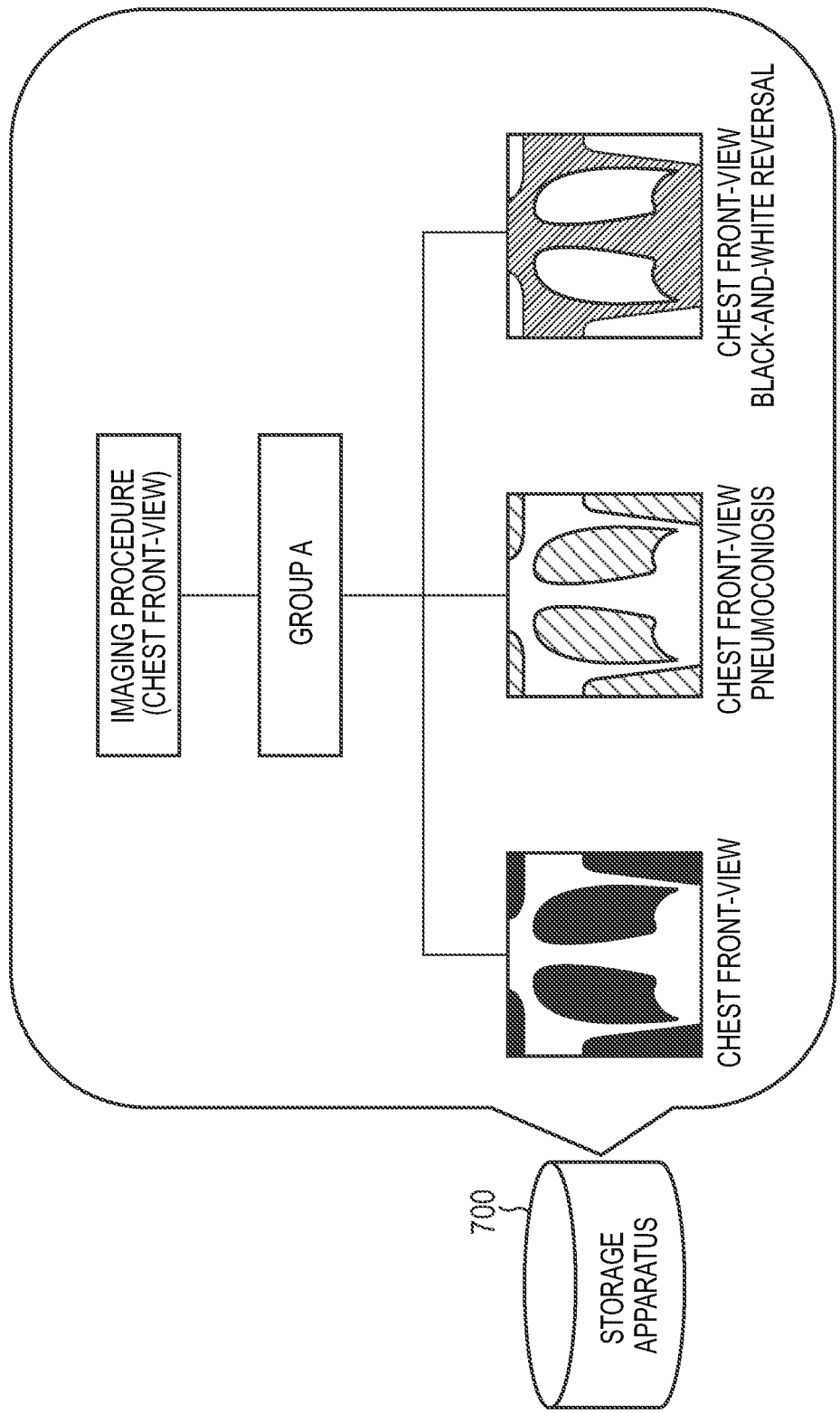
FIG. 8 is a diagram illustrating an exemplary configuration of storing radiographic images in the radiation imaging system in the present disclosure.
Figure 9:
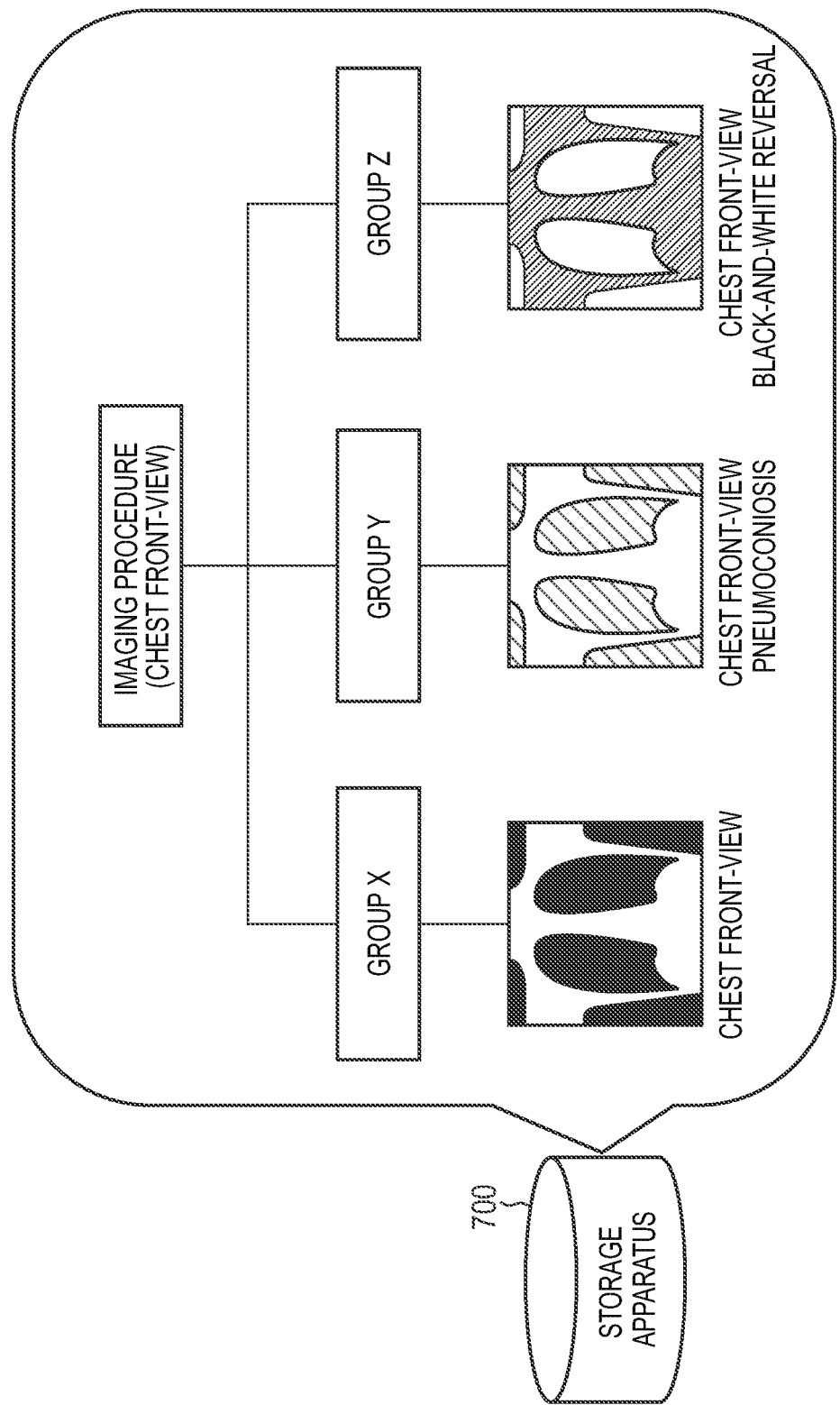
FIG. 9 is a diagram illustrating an exemplary configuration of storing radiographic images in the radiation imaging system of the present disclosure.

FIGS. 8 and 9 are diagrams illustrating configurations of storing radiographic images in the radiation imaging system. FIG. 8 illustrates a storage configuration in which the radiographic images resulting from the multiple types of image processing are associated with one another. FIG. 9 illustrates a storage configuration in which the radiographic images resulting from the multiple types of image processing are dissociated from one another.

As shown in FIG. 8, if the radiographic images resulting from the multiple types of image processing are associated with one another, the same auxiliary information (tag) is assigned to the radiographic images resulting from the multiple types of image processing. In this embodiment, the same auxiliary information (group A) is assigned to the radiographic images obtained in the chest front-view imaging procedure. The storage apparatus 700 stores the radiographic images along with the same auxiliary information (group A).

The operator can search the storage apparatus 700 by the auxiliary information to retrieve the radiographic images resulting from the multiple types of image processing. Here, based on the auxiliary information (group A), the operator can retrieve the radiographic images resulting from the normal image processing, the pneumoconiosis-specific processing, and the black-and-white reversal processing. When the operator desires to make a diagnosis using the radiographic image resulting from the pneumoconiosis-specific processing, the operator can simultaneously review the radiographic image resulting from the normal image processing.

As shown in FIG. 9, if the radiographic images resulting from the multiple types of image processing are dissociated from one another, different auxiliary information (a different tag) is assigned to each of the radiographic images resulting from the multiple types of image processing. In this embodiment, different auxiliary information (group X, group Y and group Z) is assigned to the images resulting from the respective types of image processing for the chest front-view imaging procedure. The storage apparatus 700 stores the radiographic images along with the different auxiliary information (group X, group Y and group Z)

The operator can search the storage apparatus 700 by the auxiliary information (group X) to retrieve the radiographic image resulting from the normal image processing (a single image processing). The operator can search the storage apparatus 700 by the auxiliary information (group Y) to retrieve the radiographic image resulting from the pneumoconiosis-specific processing. The operator can search the storage apparatus 700 by the auxiliary information (group Z) to retrieve the radiographic image resulting from the black-and-white reversal processing.

Figure 10:
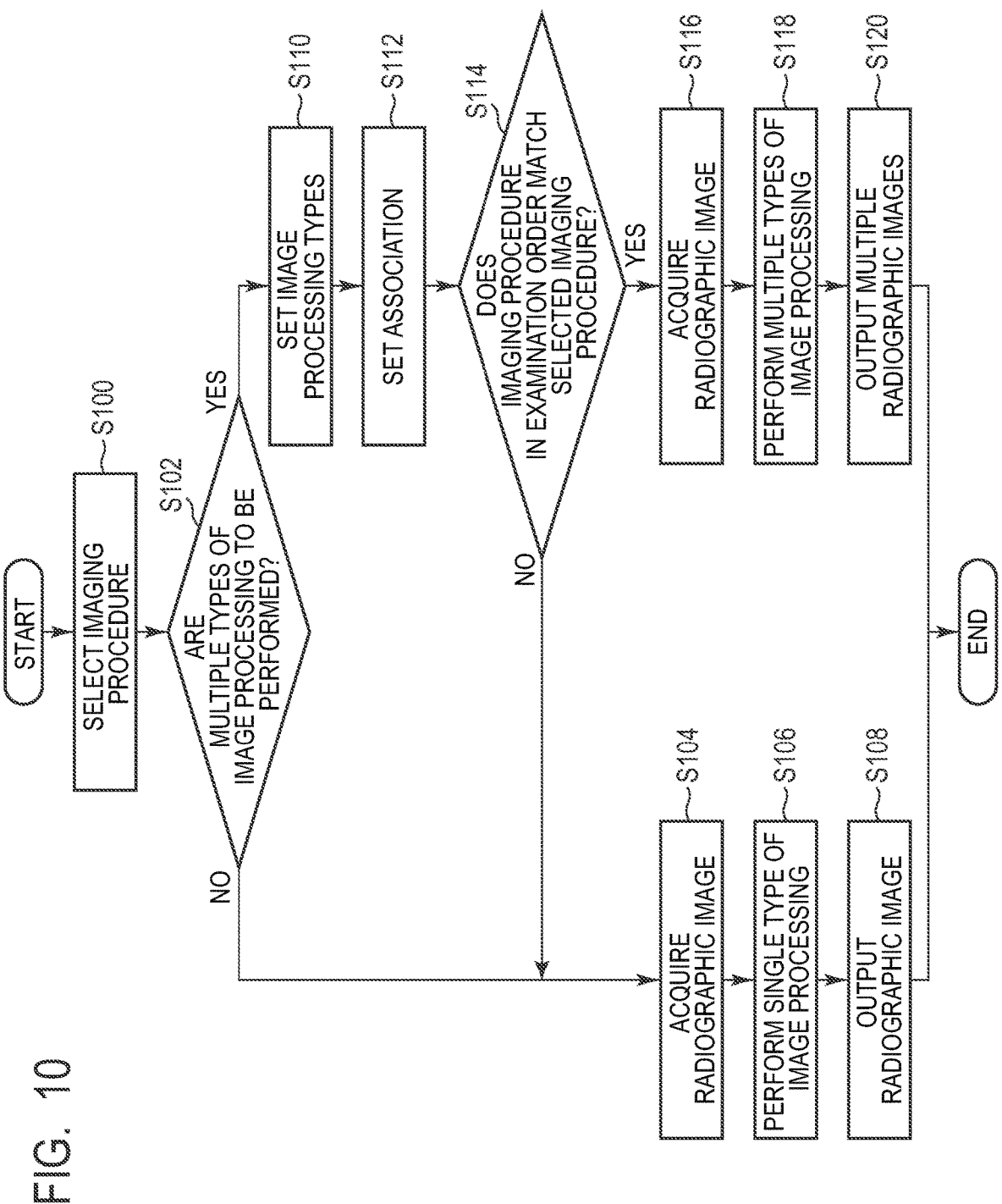
FIG. 10 is a flowchart illustrating the operations of the radiation imaging system of the present disclosure.

The operations of the radiation imaging system will now be described. FIG. 10 is a flowchart illustrating the operations of the radiation imaging system.

(step S100) Before imaging by the radiation imaging system, a specific imaging procedure is selected. For example, the operator selects "protocol name: chest front-view, sensor name: sensor A" as the imaging procedure.

(step S102) For the specific imaging procedure selected, it is determined whether multiple types of image processing are to be performed. For example, the operator determines whether to perform the black-and-white reversal processing and the pneumoconiosis-specific processing in the selected imaging procedure, in addition to the normal image processing. If multiple types of image processing are not to be performed, the process moves to step S104. If multiple types of image processing are to be performed, the process moves to step S110.

(step S104) The radiation imaging system performs imaging based on a subject's examination order sent from the RIS 132. Here, the radiation detectors 102 and 112 each image the radiation emitted from the radiation generators 100 and 110, respectively, and output a radiographic image to the image acquisition unit 200 in the control unit 120. The image acquisition unit 200 acquires the radiographic image (image data) output from each of the radiation detectors 102 and 112.

(step S106) The image processing unit 202 performs the normal image processing (such as gradation conversion for converting pixel values into intensity (luminance) values) on the radiographic image output from the image acquisition unit 200. Here, the single type of image processing is performed on the single radiographic image to generate a single radiographic image.

(step S108) The output unit 206 outputs the radiographic image resulting from the normal image processing (the single type of image processing) to the PACS (the storage apparatus) 134. The operations of the radiation imaging system for performing the normal image processing (the single type of image processing) terminates here.

(step S110) The operator, through the image processing setting unit 204, sets multiple types of image processing for the selected imaging procedure. For example, the operator determines to perform the black-and-white reversal processing and the pneumoconiosis-specific processing in the selected imaging procedure, in addition to the normal image processing.

(step S112) The association setting unit 208 sets whether the radiographic images resulting from the multiple types of image processing are to be associated with one another as a group. If the radiographic images resulting from the multiple types of image processing are to be associated with one another, the association setting unit 208 assigns the same auxiliary information (tag) to the radiographic images resulting from the multiple types of image processing.

In this manner, through steps S110 and S112, the multiple types of image processing to be performed and the association of the resultant radiographic images are set for the selected imaging procedure. This is preliminary setting before imaging.

(step S114) The control unit 120 receives the subject's examination order from the RIS 132. The control unit 120 determines whether the imaging procedure included in the subject's examination order received from the RIS 132 (the external device) matches the imaging procedure involving the multiple types of image processing. The control unit 120 here serves as a determination unit. The imaging procedure involving the multiple types of image processing is the imaging procedure selected before imaging. If the imaging procedures do not match one another, the process moves to step S104. If the imaging procedures match one another, the process moves to step S116.

(step S116) The radiation imaging system performs imaging according to the examination order sent from the RIS 132. In this embodiment, the radiation detectors 102 and 112 each image the radiation emitted from the radiation generators 100 and 110, respectively, and output a radiographic image to the image acquisition unit 200 in the control unit 120. The image acquisition unit 200 acquires the radiographic image (image data) output from each of the radiation detectors 102 and 112.

(step S118) The image processing unit 202 performs the multiple types of image processing on the radiographic image according to image processing information set by the image processing setting unit 204. For example, the image processing unit 202 performs the normal image processing, the black-and-white reversal processing, and the pneumoconiosis-specific processing on the radiographic image. In this embodiment, more than one type of image processing is performed on the single radiographic image to generate more than one radiographic image.

(step S120) If the radiographic images resulting from the multiple types of image processing are to be associated with one another, the output unit 206 outputs, along with the same auxiliary information, the radiographic images resulting from the multiple types of image processing performed by the image processing unit 202. The operations of the radiation imaging system for performing the multiple types of image processing terminates here.

As above, the radiation imaging system (a control apparatus) in the present disclosure includes: the image acquisition unit 200 that acquires radiographic images based on radiation; the image processing setting unit 204 that sets multiple types of image processing for a specific imaging procedure; an image processing unit 202 that performs the multiple types of image processing set by the image processing setting unit 204 on a radiographic image acquired in the specific imaging procedure to generate multiple radiographic images; and an association setting unit 208 that sets whether the multiple radiographic images generated by the image processing unit 202 are to be associated with one another. The association setting unit 208 can associate the multiple radiographic images generated by the image processing unit 202 with one another.

The radiation imaging system (the control apparatus) can thus store the radiographic images resulting from the multiple types of image processing in association with one another. Because the operator can retrieve the radiographic images resulting from the multiple types of image processing in an associated manner, the efficiency of diagnosis can be increased.

Second Embodiment

A second embodiment will now be described with reference to FIGS. 11 and 12. What is different from the first embodiment is that multiple storage apparatuses 710 and 712 are provided for storing radiographic images and the association setting unit 208 sets the association of the radiographic images for each of the storage apparatuses 710 and 712.

Figure 11:
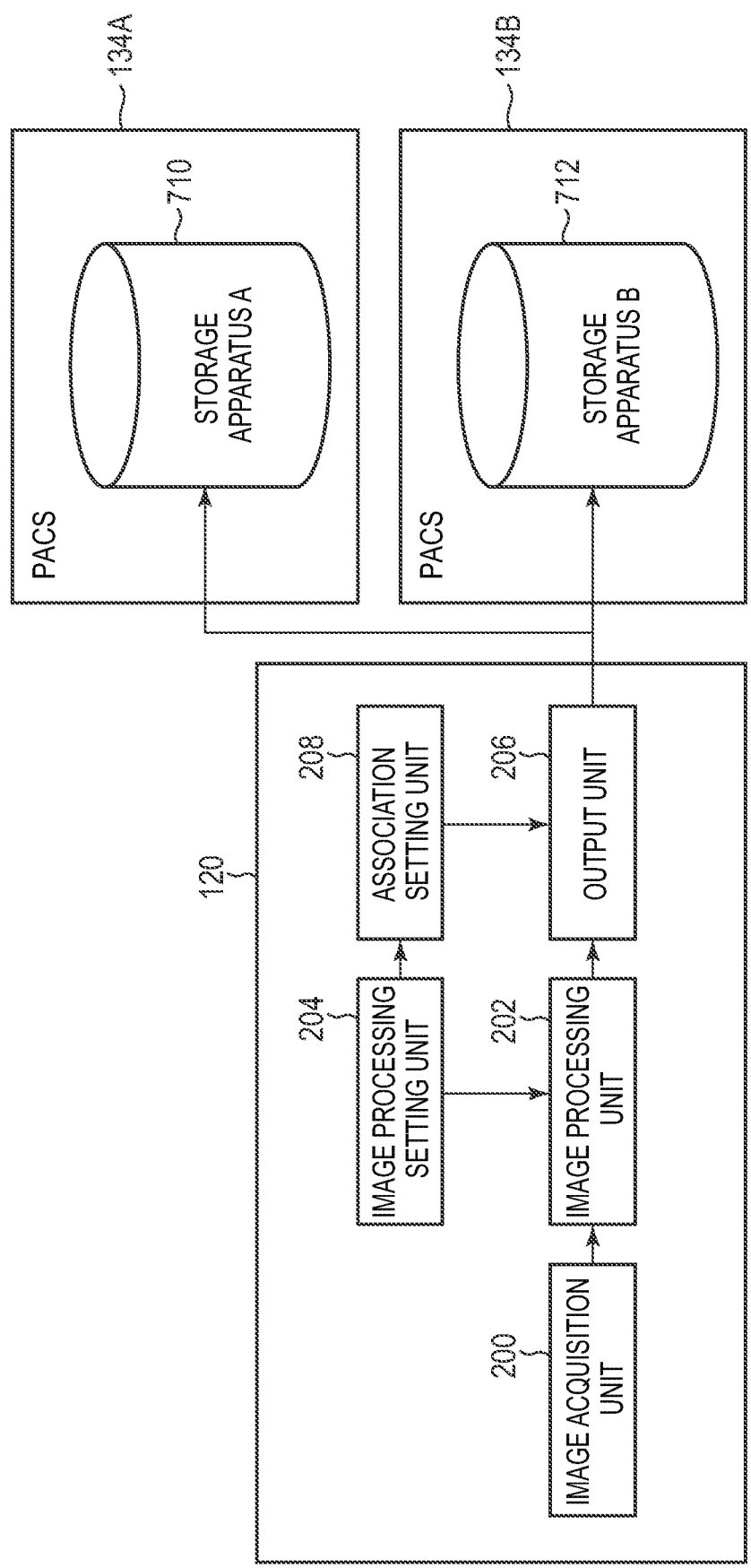
FIG. 11 is a diagram illustrating an exemplary output configuration in the radiation imaging system of the present disclosure.

FIG. 11 is a diagram illustrating a configuration of outputting radiographic images in the radiation imaging system. PACSs 134A and 134B have the function of storing all radiographic images. The PACSs 134A and 134B include the storage apparatuses 710 and 712, respectively.

Figure 12:
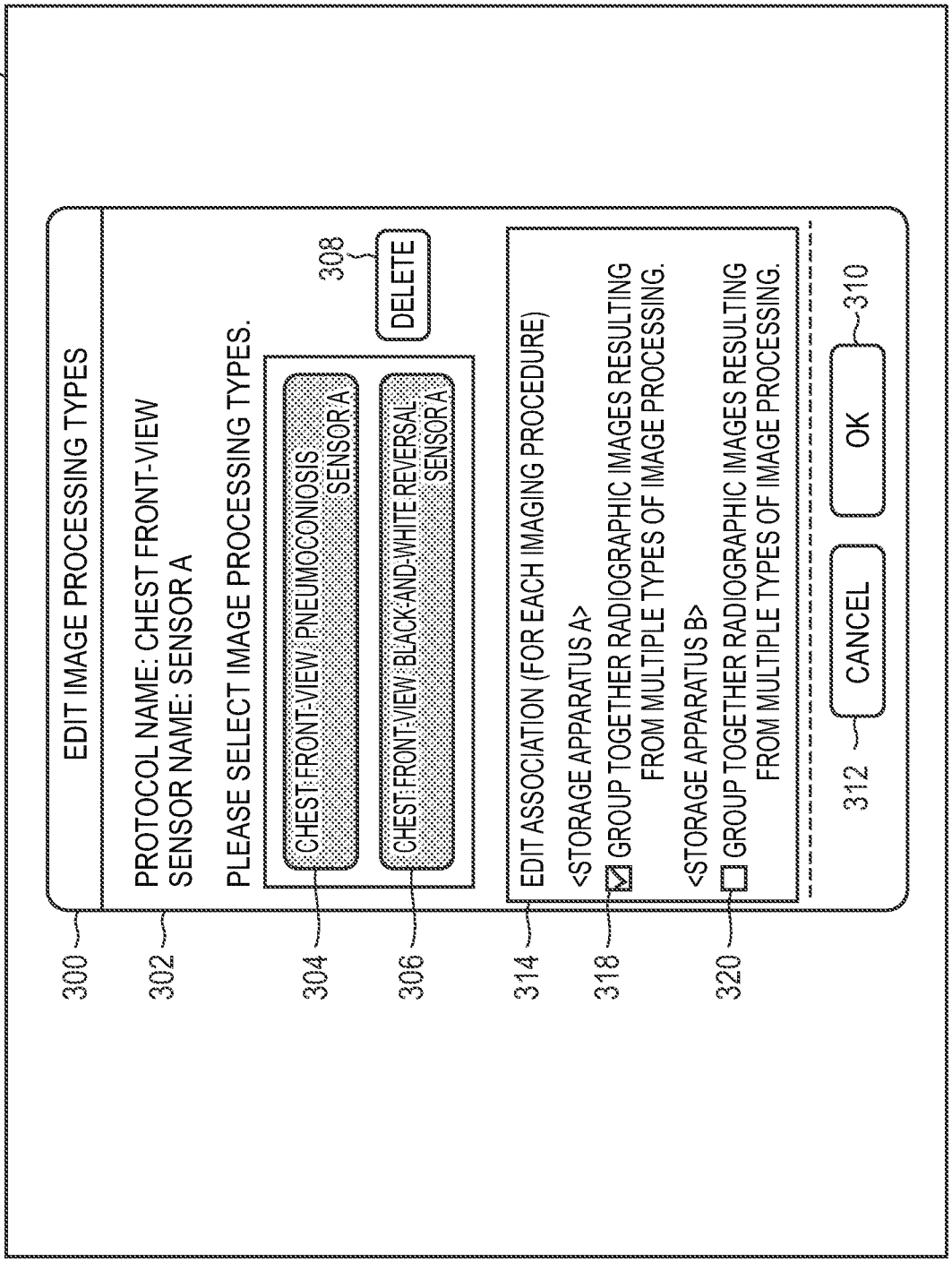
FIG. 12 is a diagram illustrating an exemplary setting screen for the image processing setting unit and the association setting unit in the radiation imaging system of the present disclosure.

FIG. 12 illustrates a setting screen for the image processing setting unit 204 and the association setting unit 208, displayed on the display unit 124. An "Edit association" menu 314 is set for each imaging procedure (the protocol name and the sensor name).

The "Edit association" menu 314 is available if multiple types of image processing are to be performed on a single radiographic image. In this embodiment, as shown in FIG. 12, the functions of the "Edit association" menu 314 are made selectable if the icon 304 for performing the pneumoconiosis-specific processing or the icon 306 for performing the black-and-white reversal processing is pressed.

The "Edit association" menu 314 shows association setting icons 318 and 320 for the respective storage apparatuses (A) 710 and (B) 712 for setting whether the radiographic images resulting from the multiple types of image processing are to be grouped together.

For the storage apparatus (A) 710, the association setting icon 318 is displayed for setting whether the radiographic images resulting from the multiple types of image processing are to be grouped together. In FIG. 12, the box of the association setting icon 318 is checked, which enables the setting of associating the radiographic images resulting from the multiple types of image processing with one another as a group.

For the storage apparatus (B) 712, the association setting icon 320 is displayed for setting whether the radiographic images resulting from the multiple types of image processing are to be grouped together. In FIG. 12, the box of the association setting icon 320 is unchecked, which enables the setting of dissociating the radiographic images resulting from the multiple types of image processing from one another as separate groups.

In this manner, the association of the radiographic images can be set for each of the storage apparatuses 710 and 712. The storage manner can therefore be configured according to the use environment of the radiation imaging system.

If the radiographic images resulting from the multiple types of image processing are associated with one another, the display unit 124 can sequentially display the radiographic images resulting from the multiple types of image processing. That is, the display unit 124 can switch to another radiographic image every predetermined time period to display the images like a multi-frame video. This allows the operator to view the radiographic images resulting from the multiple types of image processing without operating the operation unit 122.

According to the first and second embodiments, radiographic images resulting from multiple types of image processing can be stored in association with one another.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-207505, filed Nov. 2, 2018, which is hereby incorporated by reference herein in its entirety.

What is claimed is:

1. A radiation imaging system comprising:
   an image acquisition unit configured to acquire a radiographic image based on radiation;
   an image processing setting unit configured to set a plurality of types of image processing for a specific imaging procedure;
   an image processing unit configured to perform the plurality of types of image processing set by the image processing setting unit on a radiographic image acquired in the specific imaging procedure to generate a plurality of radiographic images; and
   an association setting unit configured to set whether the plurality of radiographic images generated by the image processing unit are to be associated with one another.

2. The radiation imaging system according to claim 1, wherein, if the plurality of radiographic images resulting from the plurality of types of image processing are to be associated with one another, the association setting unit is configured to assign same auxiliary information to the plurality of radiographic images resulting from the plurality of types of image processing.

3. The radiation imaging system according to claim 1, wherein, if the plurality of radiographic images resulting from the plurality of types of image processing are to be dissociated from one another, the association setting unit is configured to assign different auxiliary information to each of the plurality of radiographic images resulting from the plurality of types of image processing.

4. The radiation imaging system according to claim 1, wherein the image processing setting unit is configured to set image processing types on an imaging-procedure basis.

5. The radiation imaging system according to claim 1, further comprising a display control unit configured to cause a display unit to display radiographic images generated by the image processing unit,
   wherein the display control unit is configured to cause the display unit to display an association setting icon for setting whether the plurality of radiographic images resulting from the plurality of types of image processing are to be grouped together.

6. The radiation imaging system according to claim 5, wherein the display control unit is configured to make the association setting icon selectable if a plurality of types of image processing are to be performed on a single radiographic image.

7. The radiation imaging system according to claim 1, wherein the image processing unit is configured to perform at least one of black-and-white reversal processing and pneumoconiosis-specific processing on the radiographic image to generate a plurality of radiographic images.

8. The radiation imaging system according to claim 1, further comprising a plurality of storage apparatuses that store the radiographic images, and
   wherein the association setting unit is configured to set, for each of the plurality of storage apparatuses, association of the plurality of radiographic images with one another.

9. The radiation imaging system according to claim 1, further comprising a determination unit configured to determine whether an imaging procedure included in a subject's examination order matches the specific imaging procedure for which the plurality of types of image processing are set, and
   if the imaging procedure included in the subject's examination order matches the specific imaging procedure, the image processing unit is configured to perform the plurality of types of image processing on the radiographic image to generate a plurality of radiographic images.

10. A radiation imaging system comprising:
    an image acquisition unit configured to acquire a radiographic image based on radiation;
    an image processing setting unit configured to set a plurality of types of image processing for a specific imaging procedure;
    an image processing unit configured to perform the plurality of types of image processing set by the image processing setting unit on a radiographic image acquired in the specific imaging procedure to generate a plurality of radiographic images; and
    an association setting unit configured to associate the plurality of radiographic images generated by the image processing unit with one another.

11. A radiation imaging method, comprising:
    acquiring a radiographic image based on radiation;
    setting a plurality of types of image processing for a specific imaging procedure;
    performing the plurality of types of image processing on a radiographic image acquired in the specific imaging procedure to generate a plurality of radiographic images; and
    setting whether the plurality of radiographic images resulting from the plurality of types of image processing are to be associated with one another.

12. A non-transitory computer readable medium having stored thereon a program for causing, when executed by a computer, the computer to perform respective steps of the radiation imaging method according to claim 11.

13. A radiation imaging method, comprising:
    acquiring a radiographic image based on radiation;
    setting a plurality of types of image processing for a specific imaging procedure;
    performing the plurality of types of image processing on a radiographic image acquired in the specific imaging procedure to generate a plurality of radiographic images; and
    associating the plurality of radiographic images resulting from the plurality of types of image processing with one another.

14. A non-transitory computer readable medium having stored thereon a program for causing, when executed by a computer, the computer to perform respective steps of the radiation imaging method according to claim 13.

15. A control apparatus comprising:
    an image acquisition unit configured to acquire a radiographic image based on radiation;
    an image processing setting unit configured to set a plurality of types of image processing for a specific imaging procedure;
    an image processing unit configured to perform the plurality of types of image processing set by the image processing setting unit on a radiographic image acquired in the specific imaging procedure to generate a plurality of radiographic images; and an association setting unit configured to set whether the plurality of radiographic images generated by the image processing unit are to be associated with one another.

16. A control apparatus comprising:
an image acquisition unit configured to acquire a radiographic image based on radiation;
an image processing setting unit configured to sets a plurality of types of image processing for a specific imaging procedure;
an image processing unit configured to perform the plurality of types of image processing set by the image processing setting unit on a radiographic image acquired in the specific imaging procedure to generate a plurality of radiographic images; and
an association setting unit configured to associate the plurality of radiographic images generated by the image processing unit with one another.

\* \* \* \* \*